United States Patent [19]

Bucchianeri et al.

[11] Patent Number: 5,275,724
[45] Date of Patent: Jan. 4, 1994

[54] CONNECTOR APPARATUS AND SYSTEM

[75] Inventors: Richard Bucchianeri, Chelmsford, Mass.; Ralph Davis, Burlington, Wis.; Arthur Leuders, Mundelein; Mark Senninger, Chicago, both of Ill.

[73] Assignee: Millipore Corporation, Bedford, Mass.

[21] Appl. No.: 805,277

[22] Filed: Dec. 10, 1991

[51] Int. Cl.⁵ .............................................. B01D 61/00
[52] U.S. Cl. ................................. 210/232; 210/321.71; 251/148; 604/29; 604/258
[58] Field of Search ............... 210/232, 321.71; 422/103, 104; 137/597; 251/148; 604/29, 258, 283, 905

[56] References Cited

U.S. PATENT DOCUMENTS

| | | | |
|---|---|---|---|
| 4,096,859 | 6/1978 | Agarwal et al. | 604/29 |
| 4,298,001 | 11/1981 | Hargest, III et al. | 604/905 |
| 4,348,280 | 9/1982 | George et al. | 210/321.71 |
| 4,476,897 | 10/1984 | Morrill | 137/597 |
| 4,745,950 | 5/1988 | Mathieu | 604/29 |
| 4,968,309 | 11/1990 | Andersson | 604/905 |
| 4,969,486 | 11/1990 | Puzio | 137/597 |
| 5,141,492 | 8/1992 | Dadson et al. | 604/29 |

Primary Examiner—Robert A. Dawson
Assistant Examiner—Sun Uk Kim
Attorney, Agent, or Firm—Andrew T. Karnakis; Paul J. Cook

[57] ABSTRACT

An apparatus and a system are provided for delivering a peritoneal dialysis solution to a patient. A connector containing a first set of conduit segments and a loader containing a second set of conduit segments are mated together such as with a mating set of tracks and slots so that the two sets of conduit segments form a plurality of conduits that are each sealed from the other conduits. The loader is provided with a device for mating the conduit segments together in sealed relationship such as an eccentrically mounted rotatable cylinder and a platen in contact with the cylinder. The apparatus permits delivery of the dialysis solution to the patient and removal of the solution subsequently from the patient.

6 Claims, 9 Drawing Sheets

CONNECTOR APPARATUS AND SYSTEM

BACKGROUND OF THE INVENTION

This invention relates to a connecting means for delivering a plurality of liquid compositions through a plurality of conduits under sanitary conditions. More particularly, this invention relates to a system or apparatus for delivering a plurality of liquids to a human patient for peritoneal dialysis under sterile conditions.

Patients afflicted with end stage renal disease where kidney transplantation is unavailable must be treated either by hemodialysis or peritoneal dialysis. In peritoneal dialysis, a dialyzing liquid is introduced through an implanted tube into the patient's abdominal cavity where the peritoneum membrane functions as the dialysis membrane. The dialyzing liquid comprises an electrolyte component and a sugar component usually dextrose. The electrolyte component consists primarily of sodium chloride supplemented with calcium and magnesium salts and their function is to minimize or prevent loss of electrolyte from the patient's body across the peritoneum. The function of the sugar component is to provide an osmotic ingredient to remove water from the patient along with the normal metabolic products such as urea, uric acid and creatinine. The electrolyte and sugar solution are admixed prior to being administered and then are allowed to reside in the peritoneal cavity, usually about two hours. The solution together with the metabolic products are then removed from the patient. The electrolyte concentration is controlled to prevent electrolyte imbalance in the patient. Sugar concentration is controlled to effect removal of the metabolites while preventing dehydration of the patient.

Prior to the present invention peritoneal dialysis has been conducted by processes known as continuous cyclic peritoneal dialysis (CCPD) and continuous ambulatory peritoneal dialysis (CAPD). The latter is used by ambulatory patients often during normal work and liesure activities. Premixed electrolyte and sugar solution is located in a container that is in an elevated position relative to patient. The solution is directed into the peritoneal cavity where it remains for a period of hours. It is then drained by gravity. CAPD requires no pump.

CCPD is an automated form of CAPD wherein a solution is pumped under automated control into and from the patient a plurality of times, e.g. three times a night. The final infusion remains with the patient during the day time and is removed when initiating the next cycle. Present commercially available peritoneal dialysis systems are available from Delmed, Inc., Model 80/2; Kendall McGaw Labs Inc., Model Microstar VCI and Travenol Labs Inc., Model PAC-X.

The presently available systems all suffer from the major disadvantage that the peritoneal solutions must be stored in bags for individual administration. This requires undesirable expense in shipping and storing the unit dosage form of the stored solution. Since sanitization of the solution is effected at a location remote from the patient, there always exists the danger that the solution will become contaminated during shipping and storage.

Accordingly it would be desirable to provide a peritoneal dialysis system which does not rely upon the use of individually bagged dosage forms of the solution to be delivered to a patient. In such a system, the solution could be produced at the patient's site at the time of patient need.

SUMMARY OF THE INVENTION

The Present invention provides an interconnection apparatus for a plurality of conduits for delivering and draining liquid under sterile conditions. The apparatus includes a connector and a loader. The connector has a set of conduits linearly aligned, each having a first open end and a second open end. The first open ends are positioned on a first plane and the second open ends are positioned on a second plane. A flexible tube is connected to each of the first open ends. An aligning slot formed integrally with the connector is positioned adjacent the second open ends.

The loader includes a track which mates with the aligning slot of the connector and a platen having holes, each having a third open end and a fourth open end. The set of third open ends are positioned on the same plane and mate with the second open ends in the conduits of the connector. The set of fourth open ends are connected to a second set of conduits which, in turn direct liquid or receive liquid. Means are provided to mate the second set of open ends to the third set of open ends in sealing relationship so that there is no cross contamination between the fluids in different conduits. Means are provided in the apparatus to determine whether an electrolyte concentrate and a sugar concentrate have been properly connected for delivery to a patient.

DESCRIPTION OF SPECIFIC EMBODIMENTS

Figure 1:
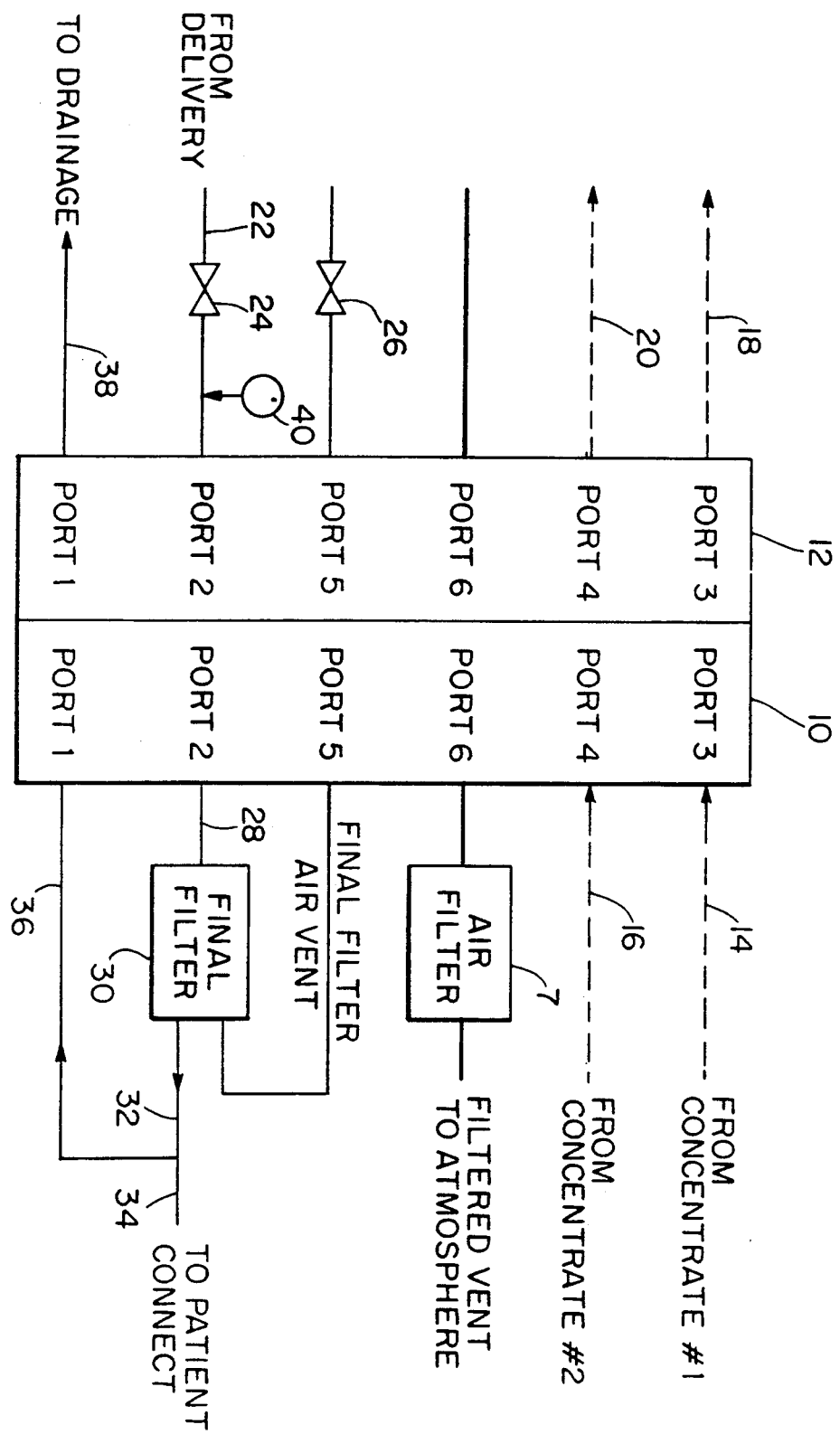
FIG. 1 is a schematic diagram illustrating the function of the apparatus of this invention.

The system of this invention is utilized in conjunction with the water purification system in a copending patent application Ser. No. 541,010, filed Jun. 20, 1990, U.S. Pat. No. 5,032,265 and entitled "Method and System for Producing Sterile Aqueous Solutions" which is incorporated herein by reference. The system of this invention also can be utilized in conjunction with the liquid proportioning means described in a copending patent application Ser. No. 561,427, filed Aug. 1, 1990, U.S. Pat. No. 5,127,542 and entitled "Process and Apparatus for proportioning Liquids" which also is incorporated herein by reference. Briefly, the water purification system referred to above is capable of purifying potable water by passing it sequentially through an ion exchange step to remove hard elements including calcium and magnesium ions; a prefilter to remove silt and particles larger than about 3 microns; an adsorption step containing activated carbon and an adsorber resin to remove bound and unbound halogens as well as organics; a reverse osmosis step which utilizes a membrane capable of withstanding temperatures up to about 100° C. and which functions in a reverse osmosis mode to remove ions, organics, colloids, suspended particles, bacteria and pyrogens, and lastly, following its mixture with concentrate compositions an ultrafiltration step to sterilize the mixture by removing all bacteria. The individual elements of the water purification system are capable of withstanding temperatures up to about 100° C. so that the entire system can be sanitized with heated water to significantly reduce accumulated bioburden within the system. The membrane utilized in the ultrafiltration step can be replaced each day as part of the disposable tubing set used in patient therapy.

The proportioning device provides a means for mixing a concentrate of the electrolyte, a concentrate of the sugar solution and the filtered water for subsequent delivery to a patient. The volumes of the concentrates are determined by measuring the static pressure at the base of a small vessel of known cross section. The small vessel has an open top and is positioned within a larger vessel. After the volumes of the concentrates are determined to be the desired volumes, the filtered water is introduced into the small vessel to cause the concentrate and the proper volume of filtered water to overflow into the larger vessel to admix the concentrate and the filtered water for delivery to the patient.

The present invention provides the interface between the patient and the systems used to form the aqueous electrolyte and sugar solutions so as to effect delivery of the solutions to the patient under filtered conditions.

The interface is formed from a conduit connector and a loader which mate with each other in sealing relationship. Each of the connector and loader has a plurality of conduit segments which are connected to form a plurality of conduits for fluid flow when the connector and loader are sealed together. The connector is slideably mounted on the loader so as to properly position the conduit segments in the connector relative to the conduit segments in the loader. Means are provided to move the conduit segments in the loader to seal with the conduit segments in the connector and to lock the conduit segments in places, sealed together. Sealing is effected with a resilient strip surrounding the mating open ends of the conduit segments in the loader which open ends are held together under pressure by pressure actuating means in the loader.

Referring to FIG. 1, the apparatus of this invention includes a connector 10 and a loader 12, each of which has six conduit segments identified as ports 1 through 6. The connector 10 and loader 12 mate in sealing relationship as will be explained more fully below. Conduits 14 and 16 are connected to ports 3 and 4 respectively of connector 10 for passage of concentrate 1 or concentrate 2 therethrough to conduits 18 and 20. Conduits 18 and 20 are connected to a proportioning device (not shown), described below wherein they are mixed with filtered water for dialysis. Conduit 22 provides a passage for the dilute electrolyte - sugar solution, when valve 24 is open and valve 26 is Closed through port 2 of connector 10 and loader 12. The dilute solution passes through conduit 28, final ultrafiltration filter 30 and through conduits 32 and 34 to the patient. When it is time to remove the solution from the patient, it is pumped though conduits 34, 36, port 1 of connector 10 and loader 12 and to metering and drainage through conduit 38. In order to test the integrity of final filter 30, air is pumped against filter 30 and the pressure decay is determined by pressure sensor 40. Port 6 is utilized to vent air from the system and to allow room air into the system.

Figure 2:
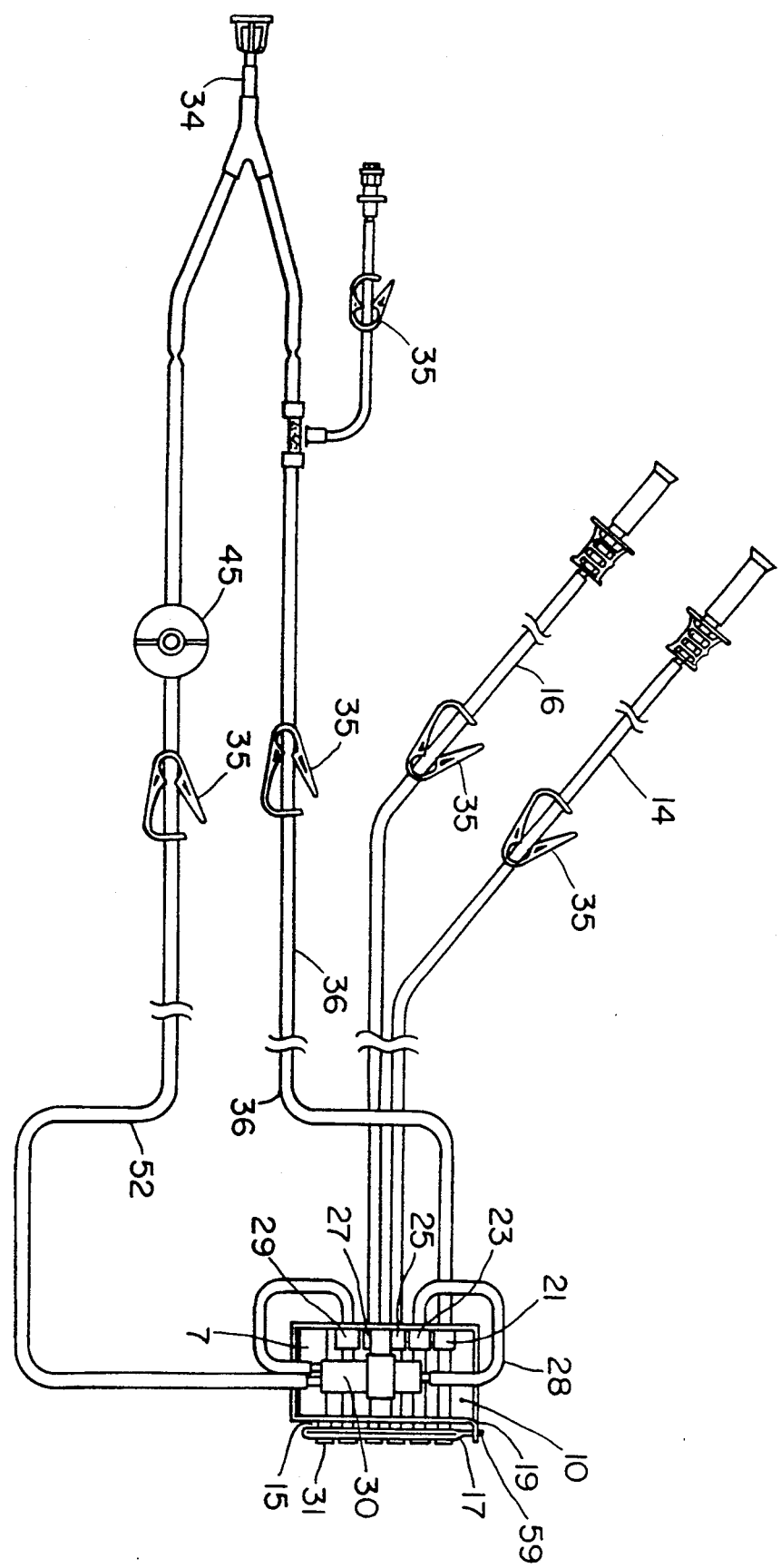
FIG. 2 is a side view of a connector with related conduits utilized in the present invention.

Referring to FIG. 2, a tubing set is shown. The entire arrangement shown in FIG. 2 is disposable after being used. The connector 10 includes a tab 59 and a slot 15 formed by rails 17 and 19. Conduit segments 21, 23, 25, 27, 29 and 31 extend through the thickness of the connector 10. Separate concentrate streams pass through conduits 14 and 16 respectively and through conduit segment 25 and 27. Each conduit 14 and 16 is provided with a shut-off clip 35. The concentrate streams pass through connector 10, through a loader (not shown), to a proportioning apparatus (not shown) where they are mixed with filtered water. The resultant liquid mixture then is passed through the loader, conduit segment 23 of connector 10, conduit 28, filter 30, and conduit 52 to the patient. Meter 45 is provided to monitor the solution volume administered to the patient. During drainage from the patient liquid passes though conduit 36 and conduit segment 21 to disposal. Conduit segment 31 is protected by filter 7 to prevent large air bourne particles from entering the system.

Figure 4:
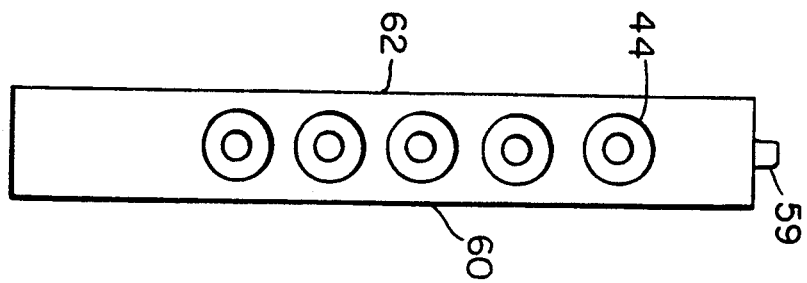
FIG. 4 is a back view of the connector of FIG. 3.
Figure 3:
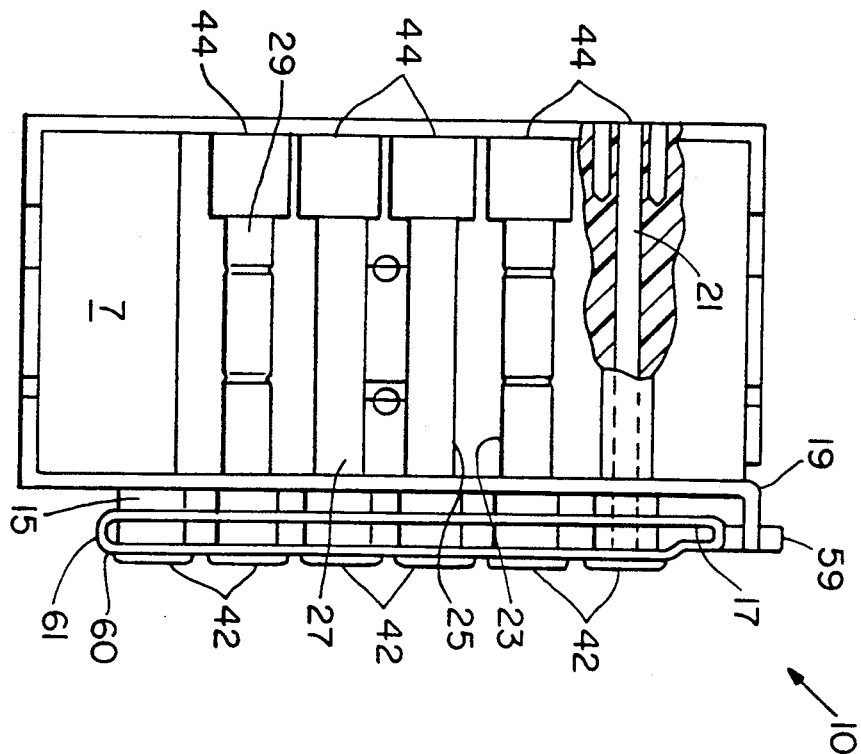
FIG. 3 is a side view, in partial cross-section of the connector portion of the apparatus of this invention.
Figure 5:
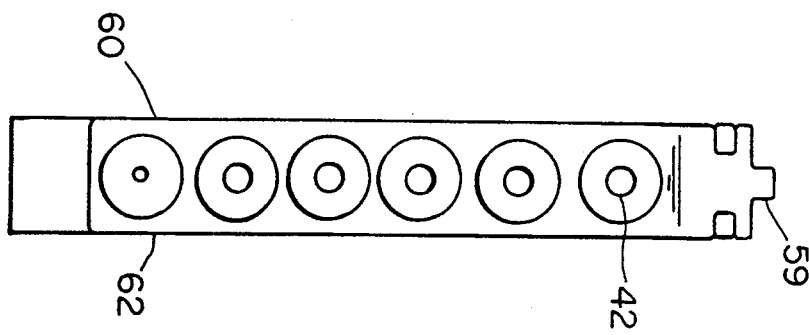
FIG. 5 is a front view of the connector of FIG. 3.

Referring to FIG. 3, 4 and 5 the connector 10 comprises a first set of open ends 42 and a second set of open ends 44. The first set of open ends 42 and a second set of open ends 44 are positioned at either end of the conduit segments 21, 23, 25, 27 and 29. Conduit 31 (FIG. 2) terminates in air filter 7. The connector 10 is provided with two slots 15 formed from rails 17 and 19 and positioned on opposing sides 60 and 62 adjacent open ends 42. The slot 15 has a curved bottom ramp 61 as part of rail 17 in order to facilitate connection to a track of loader 12 (not shown). A tab 59 is provided as a stop means as discussed below.

Figure 6:
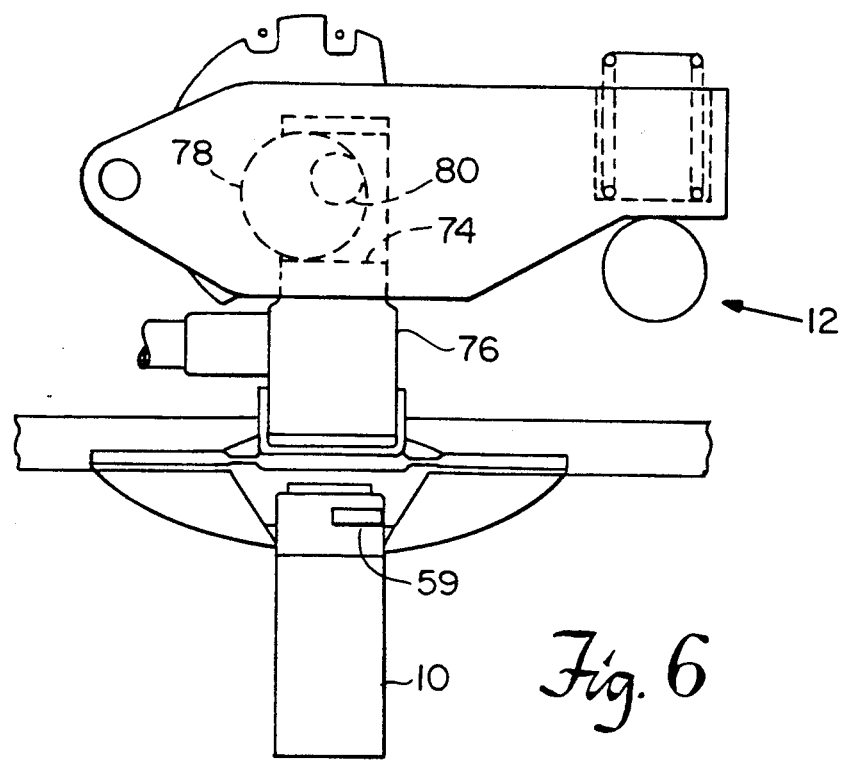
FIG. 6 is a top view of the loader and connector of this invention in the open position.

As shown in FIG. 6, the connector 10 and loader 12 are positioned together but in an unsealed relationship. The connector 10 and loader 12 are positioned together by passing the slots 15 of connector 10 (See FIGS. 7 and 8) over rails 70 (See FIGS. 7 and 9) of loader 12. The tops of rails 70 contact horizontal rails 72 of slot 15 thereby to provide a stop so that conduit segments 21, 23, 25, 27, 29 and 31 of connector 10 are positioned adjacent open ends 73 (See FIG. 9) of mating conduit segments, e.g. conduit segments 53 and 55 (See FIGS. 7 and 8) in loader 12. It is to be understood that the rails 70 can be positioned on connector 10 while the slots 15 can be positioned on loader 12 if desired. A flexible sheet 71 which has openings to expose open ends 73 (See FIGS. 7-9) is interposed between the mating open ends 73 of loader 12 and open ends 42 of connector 10.

Figure 8:
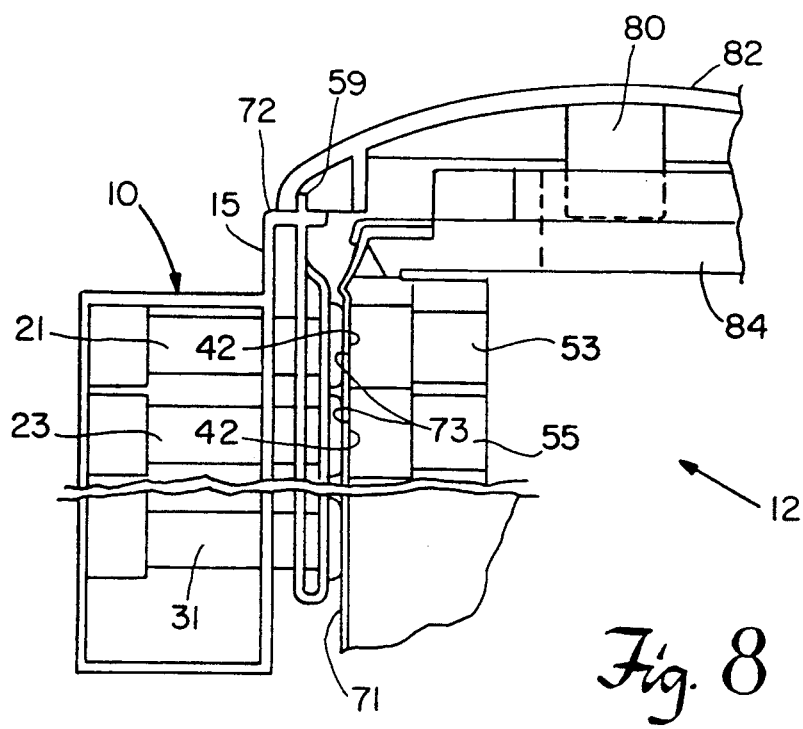
FIG. 8 is a side cross-sectional view of the loader and connector of FIG. 7.
Figure 9:
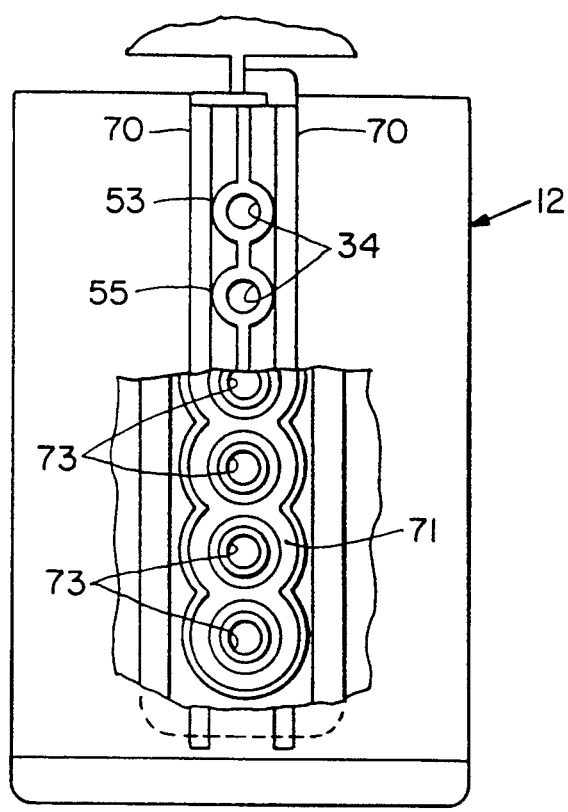
FIG. 9 is a front view in partial cross section of the broader and connector of this invention.

A means for mating the conduit segments in connector 10 and loader 12 in sealing relationship is shown in FIGS. 6 and 8. As shown in FIG. 6 a platen surface 74 on platen 76 is in contact with eccentrically mounted cylinder 78 which, in turn is connected to shaft 80 and manually operated knob 82.

Figure 7:
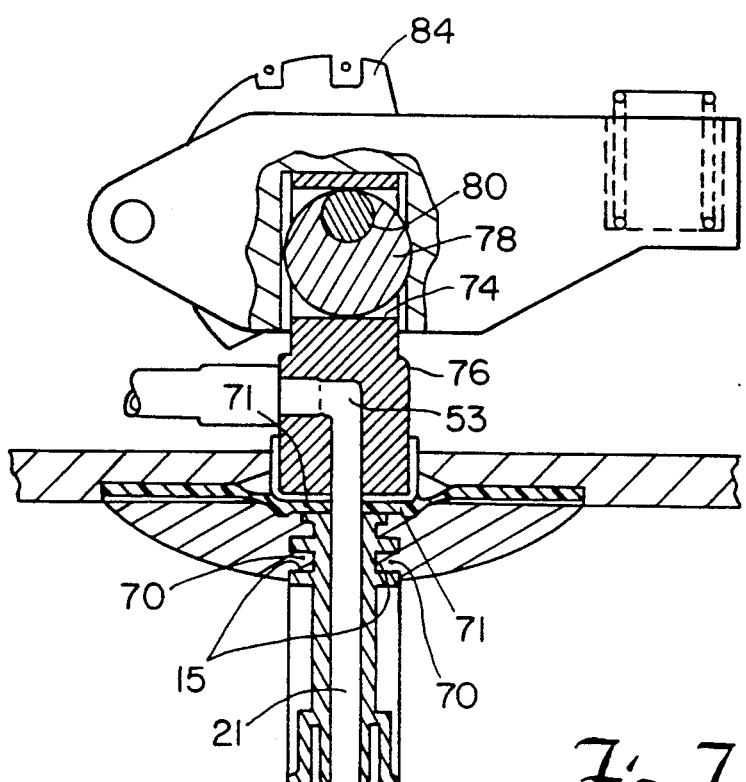
FIG. 7 is a top view in partial cross-section of the loader and connector of this invention in the closed position.
Figure 10D:
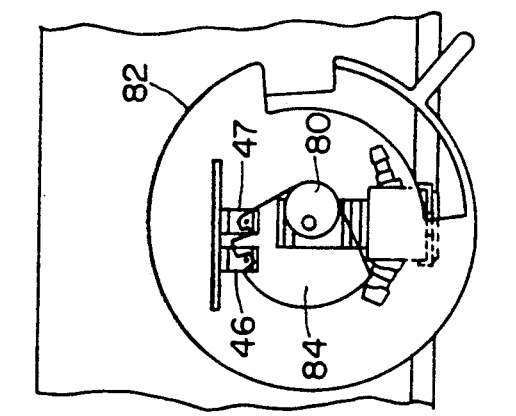
FIG. 10a, 10b, 10c and 10d illustrate safety means useful in conjunction with the apparatus of this invention.
Figure 10C:
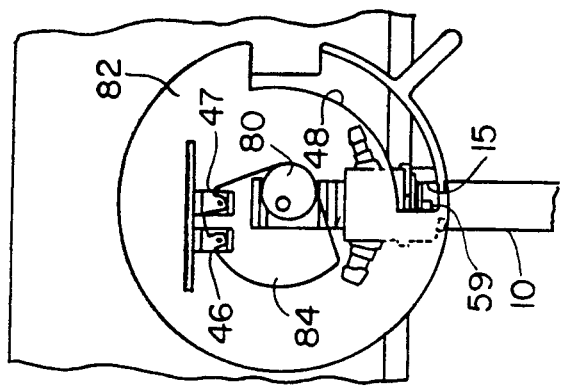
Figure 10B:
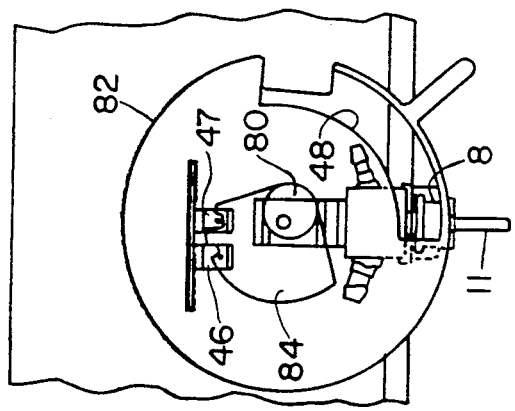
Figure 10A:
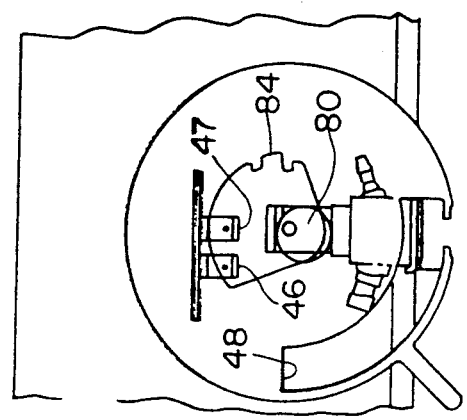

As shown in FIGS. 10a, 10b, 10c and 10d the connector 10 can be rotated to one of four positions for reasons of safety. Two optical detectors 46 and 47 are utilized to determine whether the loader 12 is open (FIG. 10a), rotated to effect sanitization of the fluid path, including loader (FIG. 10b); rotated to effect use with a patient (FIG. 10c) or rotated to an extreme and absent of any fluidic connections (FIG. 10d). The encoder plate 84 is connected to shaft 80 attached to exposed knob 82. When slot 48 is in the open position (FIG. 10a) and the open ends 42 (FIG. 5) are exposed, plate 84 blocks detector 46 and 47 so that a double negative reading indicates the position shown in FIG. 10a. In the position shown in FIG. 10b loader cover 11 which functions as a seal during sanitization include a tab 8, so shaped so that when slot 48 is rotated counterclockwise to contact tab 8, the detector 46 is blocked while detector 47 is open to indicate that sanitization is being effected. As shown in FIG. 10c, the connector 10 is placed within slot 15 of loader 12, and tab 59 extends into slot 48. Tab 59 has a different shape than tab 8 on loader cover 11 so that slot 48 extends counterclockwise to a position different than that obtained with tab 8 so that both detectors 46 and 47 are open to show that the apparatus is being used by a patient. As shown in FIG. 10d, neither the connector 10 nor the loader cover 11 is positioned within slot 15 and knob 82 is extended counterclockwise to a position where the top of slot 15 is closed. When plate 84 is in the position shown in FIG. 10d, the detector 46 is open and the detector 47 is closed which shows that slot 15 is empty and closed. As shown in FIGS. 6 and 7, cylinder 78 contacts slideably mounted platen 76 at surface 74 which causes the platen 76 containing conduit segments 53 and 55 as well as other conduit segments to contact flexible seal 71 under pressure and to cause seal 71 to effect a seal between connector 10 and loader 12 at the open ends which contact seal 72. Sealing can be effected in this manner to an elevated pressure sufficient to prevent leakage.

Figure 11:
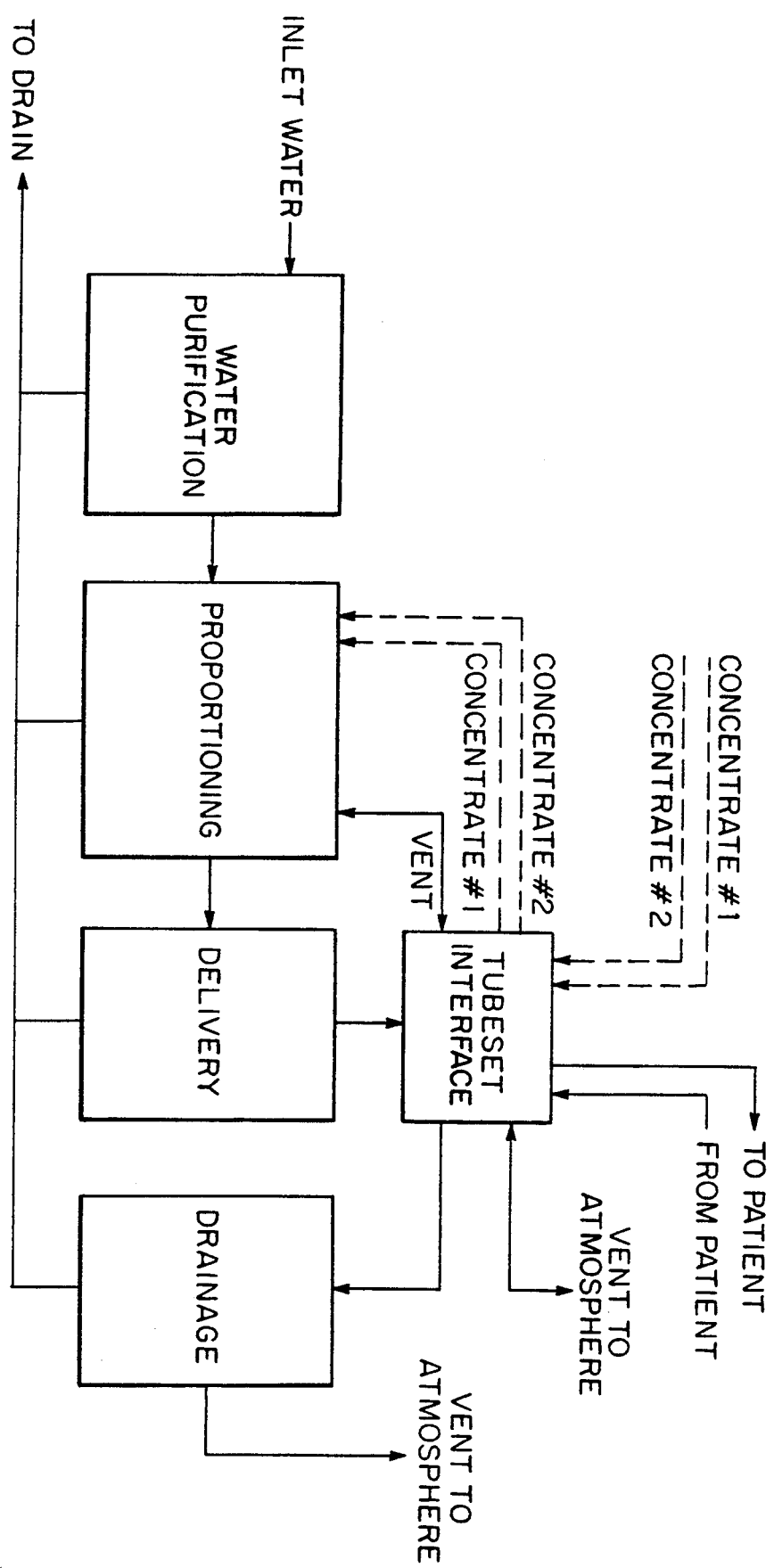
FIG. 11 is a schematic of a peritoneal dialysis system utilizing the apparatus of this invention.

As shown in FIG. 11 the connector 10 and loader 12 of this invention are identified as the tubeset interface. In FIG. 11, the concentrates 1 and 2 enter the connector portion (See FIG. 2) of the tubeset interface as to form conduits to and from the patient for solution delivery and subsequent drainage. A vent is provided for the proportioning step to the atmosphere under conditions which maintain sterility of the system such as by including in this vent line, an air filter. Examples of the proportioning function will be described below. The delivery step can comprise pump means and means to identify the nature of the solution to be delivered to the patient, such as conductivity meters which are capable of differentiating among a sugar solution, an electrolyte solution and a mixture of sugar and electrolyte solutions. The drainage system is vented to the atmosphere in order to maintain atmospheric pressure within the system.

Figure 12:
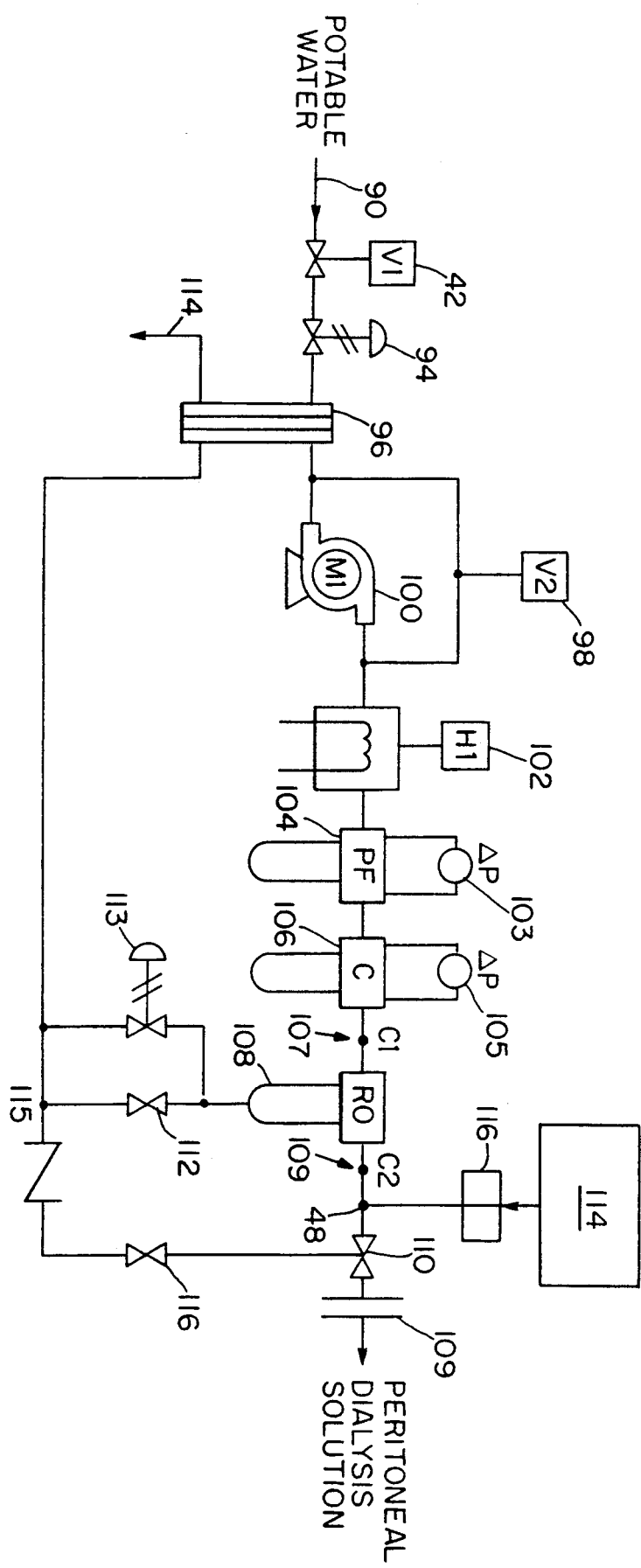
FIG. 12 is a process flow diagram of a process for producing sterile peritoneal dialysis solution for a patient useful in this invention.
Figure 13:
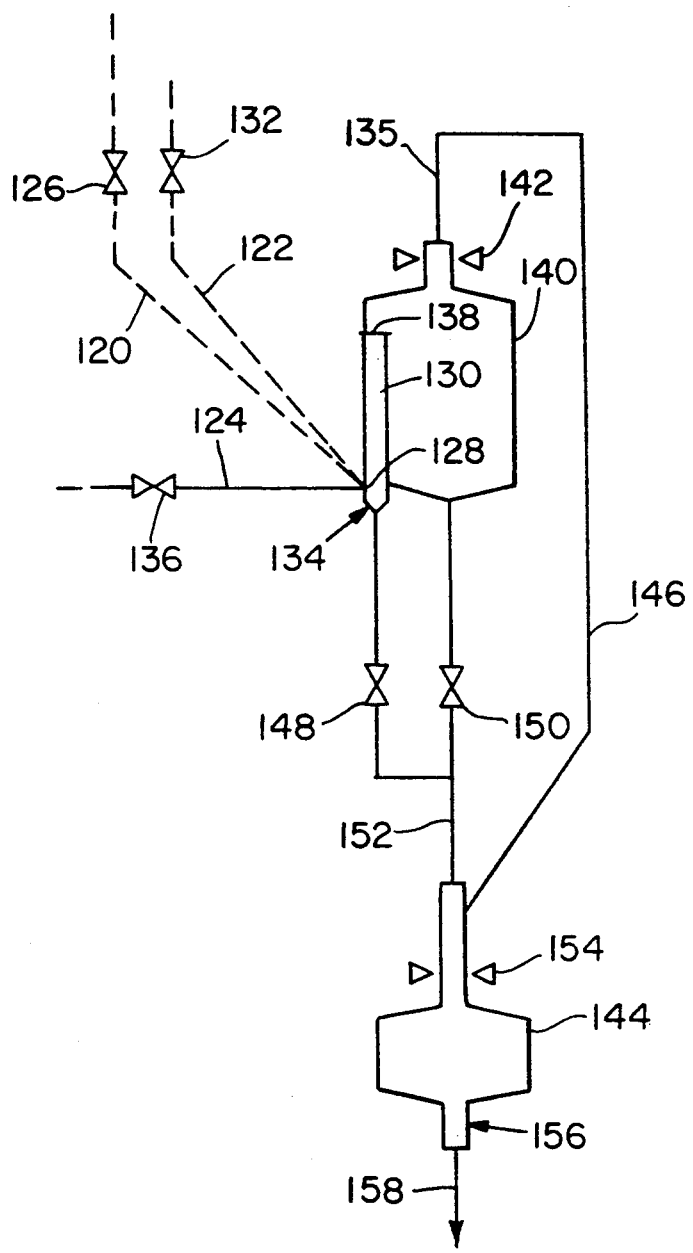
FIG. 13 is a side view of a proportioning device useful in conjunction with the present invention.

Referring to FIG. 12 a system which can be utilized in the present invention to provide sanitary water includes a water inlet 90 for potable tap water which is controlled by valve 42 and pressure regulator 94. A heat exchanger 96 is provided to recover waste heat exiting from the system during system sanitization. The tap water is pumped by means of pump 100. A bypass valve 98 is utilized during idle periods of system operation and during system sanitization when a pump may not be activated. The tap water is directed to heater 102, which may be activated to maintain a desired operating temperature of the system, to optimize the reverse osmosis module performance for production of purified water. The water is then passed through prefilter 104 which is provided with differential pressure monitor 103 which determine when the pressure across the prefilter 104 exceeds a predetermined limit. The water is then passed through an adsorption element 106 containing temperature resistant ion exchnage resin, activated carbon particles or mixtures thereof. The adsorption particles utilized in step 106 are capable of withstanding the heat of the water utilized to sanitize the system in a subsequent sanitization step. Differential pressure monitor 105 determines when the pressure across the adsorption elements exceeds a predetermined standard pressure. The filtered water then is passed to reverse osmosis unit 108 containing a temperature resistant membrane capable of withstanding the heat of the water utilized in the subsequent sanitization step. Conductivity monitors C1, C2, (107 and 109) monitor the performance of the reverse osmosis unit 108. Conductivity monitor C2 (109) also assures the quality of the water produced. The reject conduit from reverse osmosis unit 108 passes through back pressure regulator (113) which allows for adjustment of the product to reject ratio. Valve 112 remains closed during operation and is left open during sanitization since minimal back pressure is desired for the operation of the reverse osmosis unit 108 at high sanitization temperatures. The purified water is passed through valve 110 and then to use as water for dialysis. A concentrated peritoneal dialysis solution is stored in container 114 and is dispensed via proportioning module 116 into admixture with purified water from the reverse osmosis module 108. Thereafter the proportioned solution is passed through microfilter 109 for use. When the system is sanitized with water heated by heater 102, it passes through prefilter 104, adsorption unit 06, reverse osmosis unit 100 and then splits to valve 112 on reject conduit side and valve 116 on product side while valve 10 remains closed during sanitization. The water from reject conduit side and valve 116 are combined at location 115 and passed through heat exchanger 96 to recover heat prior to passing to drain 114. The heater 102 then is deactivated at the completion of sanitization and the system is flushed of the heated water by means of incoming potable water. The proportioning module 116 ca be included in the high temperature sanitization loop to maintain control of bacteria and pyrogens. In the proportioning arrangement shown in FIG. 13, three liquid components can be delivered through conduits 120, 122 and 124 for a first liquid concentrate, a second liquid concentrate and purified filtered water, respectively. In a first step, valve 126 is opened so that the first concentrate enters inlet 128 to subchamber 130 to partially fill subchamber 30. Pressure sensor 134 measures the static pressure of the first concentrate. Since the dimension of the subchamber 130 and the density of the first concentrate are known, the pressure measurement obtained gives the operator sufficient information as to whether the correct volume of the first liquid concentrate is present in subchamber 130. After it has been determined so that the correct volume of the first concentrate is present in subchamber 130, valve 126 is closed and valve 132 is opened to permit the second concentrate to pass through conduit 122 and inlet 128 into subchamber 130. The sum of the volumes of the second concentrate and the first concentrate is less then the subchamber volume so that a pressure measurement can be observed with pressure sensor 134 to determine whether the correct amount of the second concentrate is present in subchamber 130 in the manner set forth above. Valve 132 then is closed and valve 136 is opened to permit the purified water to pass through conduit 124 and inlet 128 to enter subchamber 130, overflow through outlet 138 into chamber 140 prior to the level sensed by level sensor 142. Since the densities of the first and second concentrates and the purified water are known, as is the height of the subchamber 130 to the overflow point, a pressure measurement obtained with pressure sensor 134 can be utilized to determine whether drift has occurred in pressure sensor 134 and whether the measurements are accurate. It is to be noted that both chamber 140 and reservoir 144 are vented to the atmosphere by means of conduits 135 and 146, each of which can contain an air filter to prevent microbiological contamination of the system. Valves 148 and 150 then are opened so that liquid in chamber 140 and subchamber 130 can pass through conduit 152 into reservoir 144. The reservoir 144 is provided with a level sensor 154 to detect an overfill of the volume of liquid in the reservoir 144. The pressure sensor 156 is utilized to measure the volume of liquid composition of known density in the reservoir 144 of known dimensions. The liquid from reservoir 144 then is delivered for use through conduit 158.

We claim:

1. Apparatus for connecting in sealed relationship a connector means for passing a plurality of fluids in separate conduits and loader means for passing a plurality of fluids, said loader means being connected to means for delivering a filtered fluid which comprises said connector means comprising a housing containing a plurality of a first set of conduit segments, said first set of conduit segments having a first set of open ends and a second set of open ends, said loader means containing a plurality of a second set of conduit segments, said second set of conduit segments having a third set of open ends and a fourth set of open ends, means to position said second set of open ends adjacent said third set of open ends, an elastic sealing means positioned between said second set of open ends and said third set of open ends and adapted to maintain fluid communication between said first set of open ends and said fourth set of open ends, and means to contact a portion of said loader means surrounding said third set of open ends and a portion of said connector means surrounding said second set of open ends against said elastic sealing means under pressure thereby to effect fluid communication between each member of said first set of conduit segments with only one member of said second set of conduit segments.

2. The apparatus of claim 1 wherein said means to position comprises tracks on one of said connector means or of said loader means and slots which mate with said tracks on the other of said connector means or loader means.

3. The apparatus of claim 1 wherein said means to contact comprises an eccentrically mounted rotatable means adapted to move a platen containing said second set of conduit segments when said rotatable means is rotated.

4. The apparatus of any one of claim 1, 2 or 3 wherein individual conduit segments of said first set of conduit segments of said connector means are connected respectively to a first filtered concentrate solution, a second concentrate solution, a dilute peritoneal dialysis solution for delivery to a patient and a drainage conduit for removal of said peritoneal dialysis solution from said patient.

5. The apparatus any one of claims 1, 2 or 3 including means to sanitize water and means to proportion (a) sanitized water, (b) a first filtered concentrate and (c) a second filtered concentrate and wherein said individual conduit segments of said second set of conduits of said loader means are connected respectively to said first filtered concentrate solution from said connector means; said second filtered concentrate from said connector means; a dilute sanitary solution containing said first filtered concentrate and said second filtered concentrate from means to sanitize water and means to proportion said (a) sanitized water, (b) said first filtered concentrate and (c) said second filtered concentrate; and a drainage solution from said connector means.

6. A disposable connector apparatus having a first set of conduit segments for sealing engagement with a second set of conduit segments, one of said first set of conduit segments being connected to a first concentrate solution, a second conduit segment of said first set being connected to a second concentrate solution, a third conduit segment of said first set being connected to a filtered dialysis solution, a fourth conduit segment of said first set being connected to a drainage solution and sealing means to engage said first set of conduit segments to a second set of conduit segments thereby to effect fluid communication between each member of said first set of conduit segments with only one member of said second set of conduit segments.

* * * * *